(12) United States Patent
Choi et al.

(10) Patent No.: US 11,253,678 B2
(45) Date of Patent: Feb. 22, 2022

(54) MULTI-CURVATURE CATHETER AND MEDICAL DEVICE FOR SURGERY

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jae Soon Choi, Seoul (KR); Young Jin Moon, Seoul (KR); Gi Byoung Nam, Seoul (KR); Young Hak Kim, Seoul (KR); Zhenkai Hu, Seoul (KR); Ho Yul Lee, Paju-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 213 days.

(21) Appl. No.: 16/530,005

(22) Filed: Aug. 2, 2019

(65) Prior Publication Data

US 2019/0351190 A1 Nov. 21, 2019

Related U.S. Application Data

(63) Continuation of application No. PCT/KR2018/001894, filed on Feb. 13, 2018.

(30) Foreign Application Priority Data

Feb. 17, 2017 (KR) .................. 10-2017-0021831

(51) Int. Cl.
*A61M 25/01* (2006.01)

(52) U.S. Cl.
CPC .... *A61M 25/0147* (2013.01); *A61M 25/0136* (2013.01); *A61M 25/0144* (2013.01);
(Continued)

(58) Field of Classification Search
CPC .......... A61M 25/0147; A61M 25/0136; A61M 25/0144; A61M 25/0152;
(Continued)

(56) References Cited

U.S. PATENT DOCUMENTS

| | | |
|---|---|---|
| 5,254,088 A | 10/1993 | Lundquist et al. |
| 5,314,466 A | 5/1994 | Stern et al. |

(Continued)

FOREIGN PATENT DOCUMENTS

| | | |
|---|---|---|
| JP | H07-213618 A | 8/1995 |
| JP | H08-19618 A | 1/1996 |

(Continued)

OTHER PUBLICATIONS

International Search Report issued in PCT/KR2018/001894; dated May 30, 2018.

(Continued)

*Primary Examiner* — Manuel A Mendez
(74) *Attorney, Agent, or Firm* — Studebaker & Brackett PC

(57) ABSTRACT

A catheter and a surgical medical device. The catheter includes at least; a first elastic member positioned at an end portion of the catheter: a second elastic member connected with the first elastic member, the second elastic member being curved with a first radius of curvature to protrude toward a first direction; a first wire connected with a first surface of the first elastic member, and configured to pull the catheter to bend the catheter in the first direction; a second wire connected with a second surface of the first elastic member, which is opposite to the first surface, and configured to pull the catheter to bend the catheter in a second direction; and a tube containing the first elastic member, the second elastic member, the first wire, and the second wire.

20 Claims, 11 Drawing Sheets

(52) U.S. Cl.
CPC . *A61M 25/0152* (2013.01); *A61M 2025/0161* (2013.01); *A61M 2025/0163* (2013.01)

(58) Field of Classification Search
CPC .. A61M 2025/0161; A61M 2025/0163; A61M 2025/0166; A61M 25/0041; A61M 2230/10; A61M 25/0074; A61M 25/0133; A61M 2025/0095; A61M 25/0141; A61M 25/0054; A61M 2205/0216; A61B 5/283; A61B 5/24; A61N 1/05
See application file for complete search history.

(56) References Cited

U.S. PATENT DOCUMENTS

| | | | |
|---|---|---|---|
| 5,782,828 A | | 7/1998 | Chen et al. |
| 2002/0068868 A1* | | 6/2002 | Thompson ........ A61M 25/0152 600/434 |
| 2004/0122417 A1* | | 6/2004 | Rabiner ............ A61M 25/0069 604/528 |

FOREIGN PATENT DOCUMENTS

| | | |
|---|---|---|
| JP | 2006-255401 A | 9/2006 |
| JP | 5618471 B2 | 11/2014 |
| KR | 10-2011-0139698 A | 12/2011 |

OTHER PUBLICATIONS

The extended European search report issued by the European Patent Office dated Jan. 23, 2020, which corresponds to European Patent Application No. 18754832.6-1132 and is related to U.S. Appl. No. 16/530,005.

* cited by examiner

MULTI-CURVATURE CATHETER AND MEDICAL DEVICE FOR SURGERY

CROSS-REFERENCE TO RELATED APPLICATIONS

The present application is a continuation of International Patent Application No. PCT/KR2018/001894, filed Feb. 13, 2018, which is based upon and claims the benefit of priority to Korean Patent Application No. 10-2017-0021831, filed on Feb. 17, 2017. The disclosures of the above-listed applications are hereby incorporated by reference herein in their entirety.

BACKGROUND

Embodiments of the inventive concept described herein relate to a catheter and a surgical medical device, and more particularly, to a catheter configured to be bent as a wire is adjusted, and a surgical medical device having the same catheter.

A catheter is a device collectively referred to as a medical device that is directly inserted into a human body. Various catheters have been used for insertion into the human body, like vascular injection, coronary artery dilatation, urethra insertion, airway insertion, or laparoscopic surgery.

The catheter has to be inserted precisely through a vessel, urethra, or airway and has to be finely adjusted. Accordingly, the catheter has to be precisely manufactured, and the improvement of the catheter is more required in terms of the convenience of operation, accuracy, and stability.

In addition, various catheters have been developed and angioplasty procedures have been developed in cardiovascular therapy fields such as the stroke due to the blockage of a cerebral vessel or a coronary artery, an acute myocardial infarction, or a heart attack.

Recently, a catheter has been developed to manipulate the introduction direction into a body cavity by bending the distal end of the catheter.

For example, Korean Unexamined Patent Publication No. 10-2011-0139698 (published on Dec. 29, 2011) discloses a catheter and a method for manufacturing the catheter. That publication describes a catheter in which a pass-through wire (manipulating line) having specific stiffness is provided in a catheter body (tubular body), and the manipulating line is pushed, so the distal end of the tubular body is bent. Likewise, catheters to be introduced into a body cavity as the distal end of the catheter is adjustable by the manipulating line are developed recently.

SUMMARY

Embodiments of the inventive concept provide a catheter capable of forming various bending curvatures by allowing a bending portion to be started to bend at different points depending on the bending directions of the catheter, and a surgical medical device including such a catheter.

Embodiments of the inventive concept provide a catheter configured to be variously bent by the combination of a plurality of elastic members different from each other in length, curvature, or bending direction, and a surgical medical device including such a catheter.

Embodiments of the inventive concept provide a catheter capable of applying a force greater than the force applied from the outside by winding a wire up several times using pulleys and of realizing various catheter motions by connecting a plurality of bending sections with each other, and a surgical medical device including such a catheter.

The objects which will be achieved in the inventive concept are not limited to the above, but other objects, which are not mentioned, will be apparently understood to those skilled in the art.

According to some embodiments of the present disclosure, a catheter includes: a first elastic member positioned at an end portion of the catheter; a second elastic member connected with the first elastic member, the second elastic member being curved with a first radius of curvature to protrude toward a first direction; a first wire connected with a first surface of the first elastic member, and configured to pull the catheter to bend the catheter in the first direction; a second wire connected with a second surface of the first elastic member, which is opposite to the first surface, and configured to pull the catheter to bend the catheter in a second direction; and a tube containing the first elastic member, the second elastic member, the first wire, and the second wire.

According to some embodiments of the present disclosure, a surgical medical device includes: a catheter; and a driving device. The catheter of the surgical medical device includes: a first elastic member positioned at an end portion of the catheter, a second elastic member connected with the first elastic member, the second elastic member being curved with a first radius of curvature to protrude toward a first direction; a first wire connected with a first surface of the first elastic member; a second wire connected with a second surface of the first elastic member, which is opposite to the first surface; a tube containing the first elastic member, the second elastic member, the first wire, and the second wire; and an electrode exposed to an outside of the catheter. The driving device of the surgical medical device is provided outside the catheter and configured to control pulling degrees of the first wire and the second wire to bend the catheter in the first direction or a second direction, which is opposite to the first direction.

BRIEF DESCRIPTION OF DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
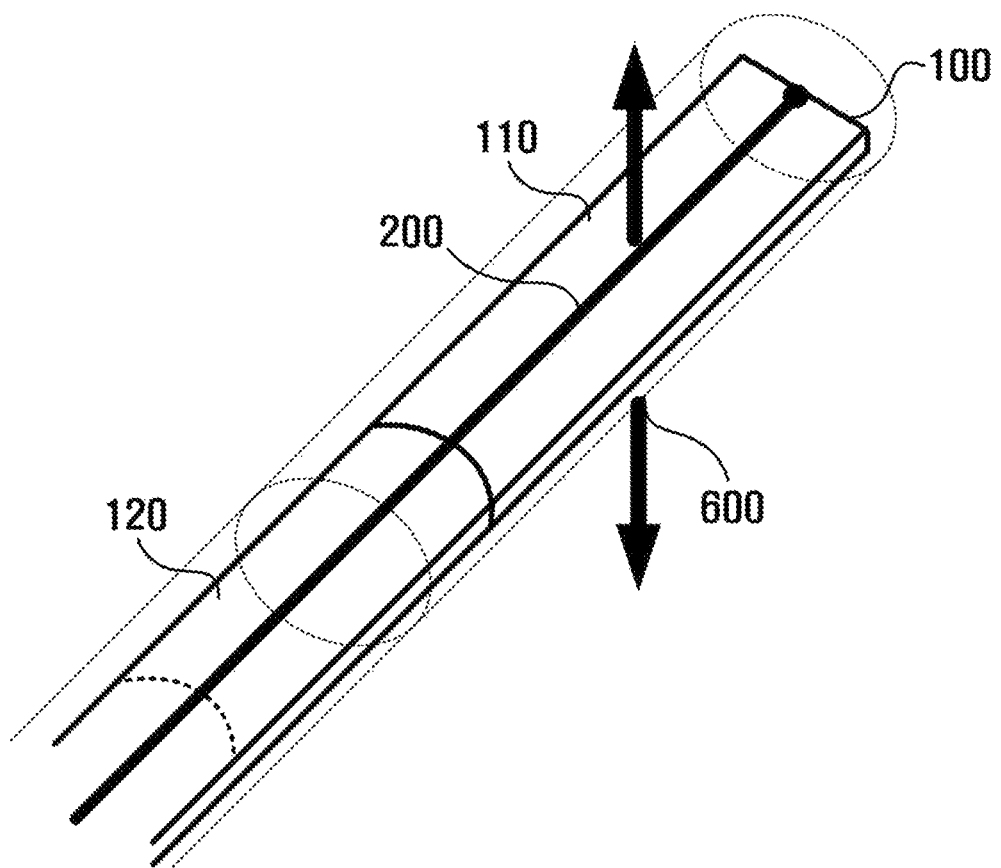
FIG. 1 is a view illustrating a catheter according to some embodiments of the present disclosure.

Hereinafter, exemplary embodiments of the inventive concept will be described with reference to accompanying drawings. Advantage points and features of the prevent invention and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. The inventive concept may be defined by the scope of the claims. Meanwhile, the terminology used herein to describe embodiments of the invention is not intended to limit the scope of the inventive concept. Like reference numerals refer to like elements throughout the whole specification.

Unless otherwise defined, all terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used in the inventive concept is provided for the illustrative purpose, but the inventive concept is not limited thereto. As used herein, the singular terms "a," "an" and "the" are intended to include the plural forms as well, unless the context clearly indicates otherwise. Furthermore, it will be further understood that the terms "comprises", "comprising." "includes" and/or "including", when used herein, specify the presence of stated elements, steps, operations, and/or devices, but do not preclude the presence or addition of one or more other components, steps, operations and/or devices.

FIG. 1 is a view illustrating a catheter according to some embodiments of the present disclosure.

Figure 2:
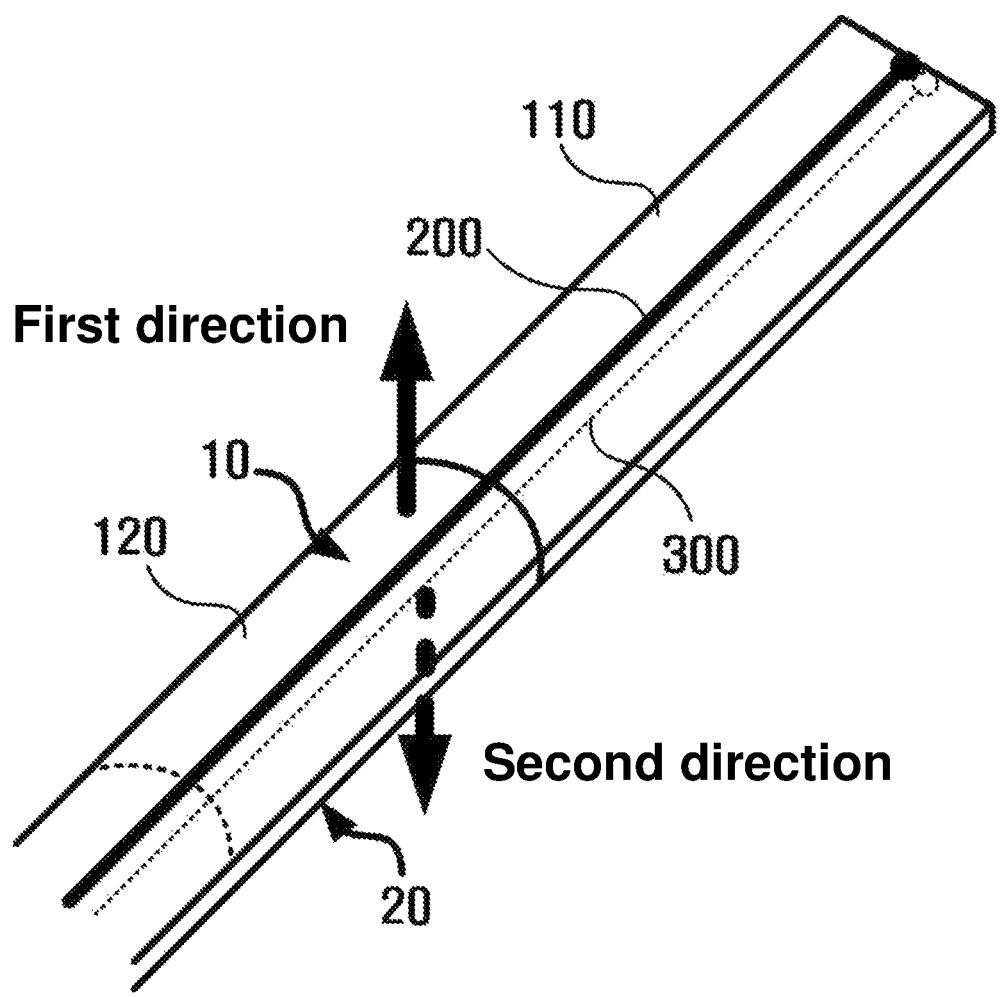
FIGS. 2, 3A and 3B are views illustrating a bending section including a first elastic member provided in a flat form, according to some embodiments of the present disclosure.

Referring to FIGS. 1 and 2, according to some embodiments of the present disclosure, the catheter includes a bending section 100, a first wire 200, a second wire 300, and a tube 600.

Figure 5:
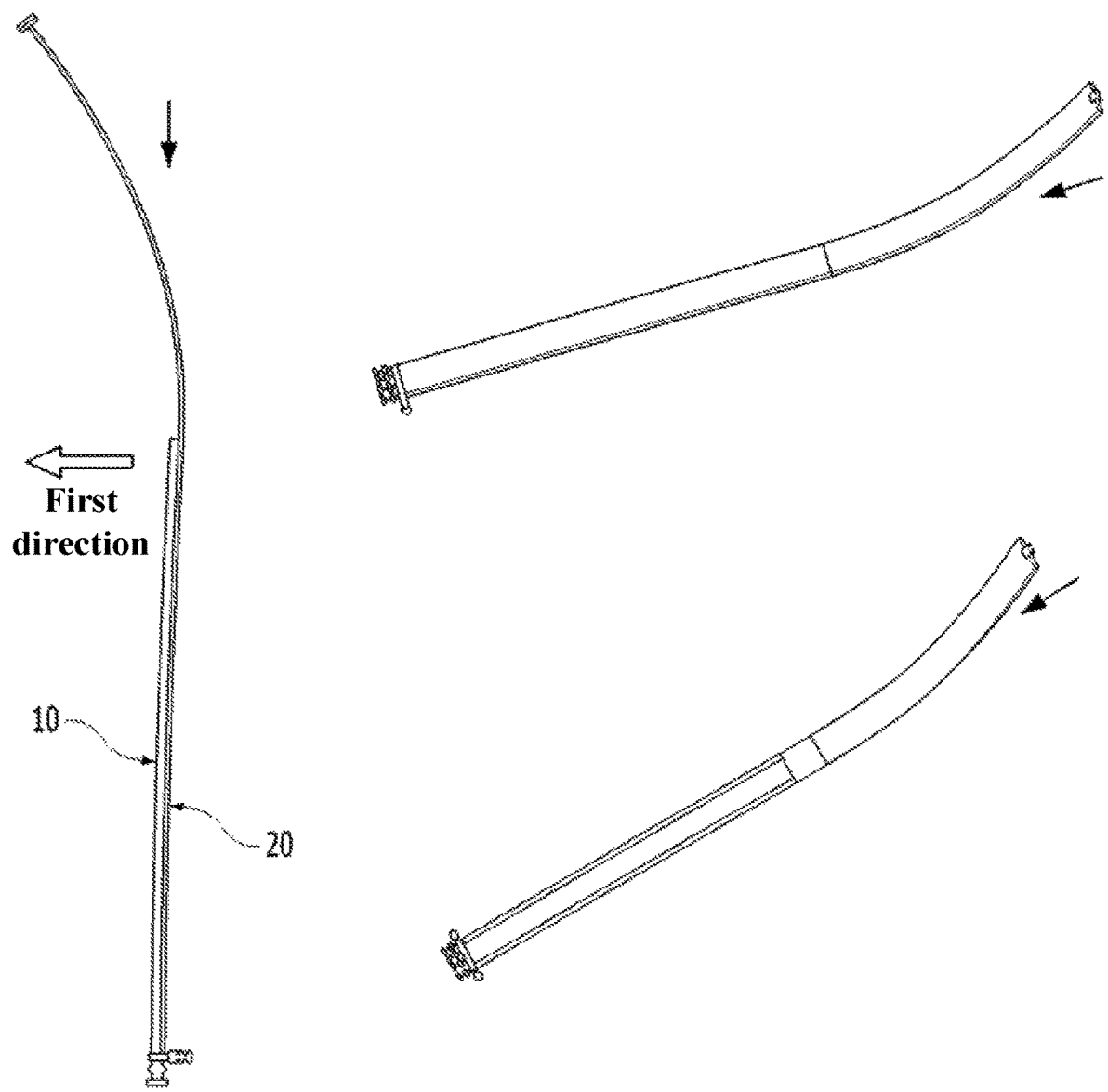
FIG. 5 is a view illustrating a bending section pulled in a first direction according to some embodiments of the present disclosure.
Figure 6:
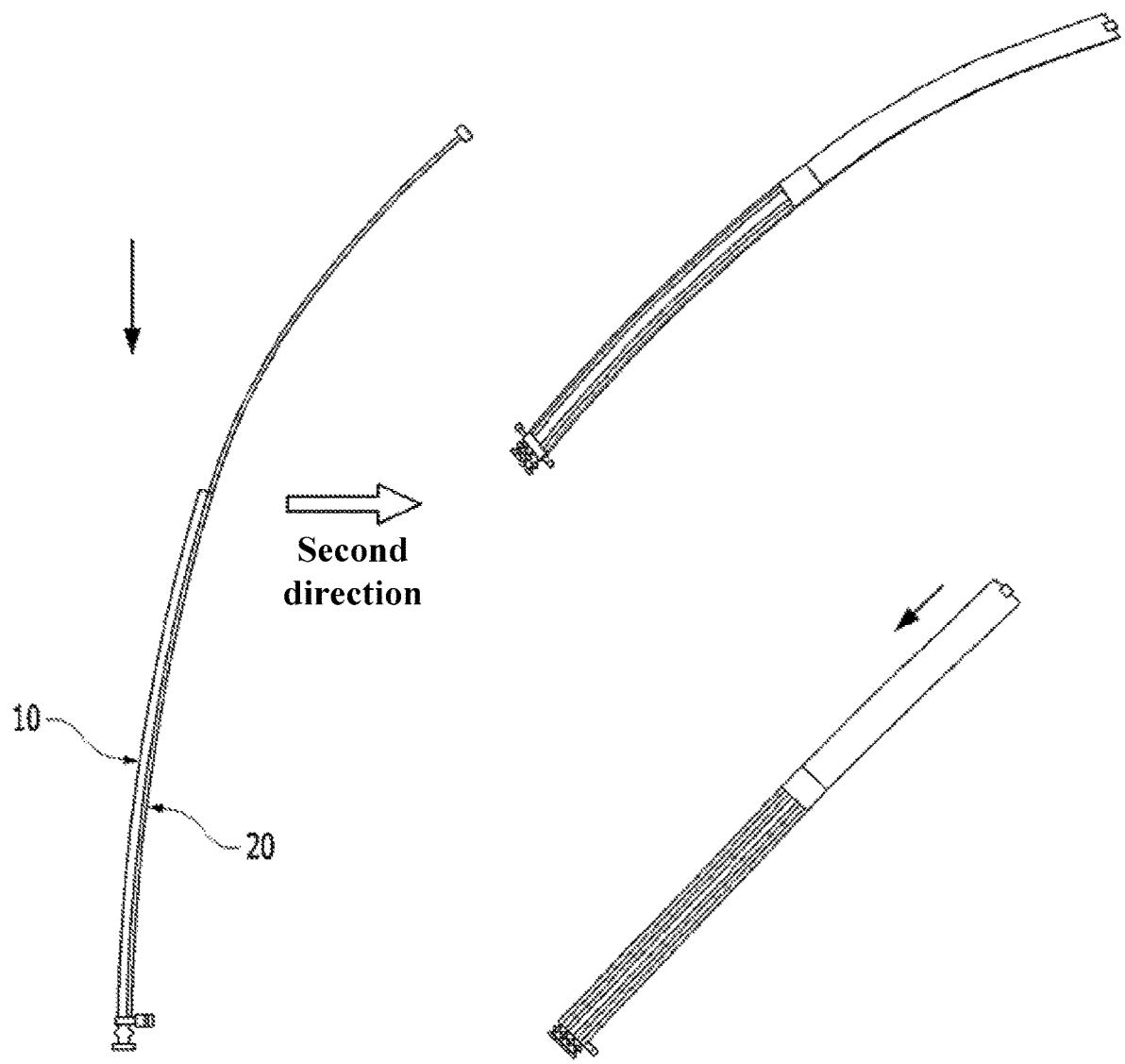
FIG. 6 is a view illustrating a bending section pulled in a second direction according to some embodiments of the present disclosure.

The bending section 100 corresponds to a component to bend the catheter after the catheter being inserted into a human body. Since the bending section has a particular width and a particular thickness, the bending section is bent through the manipulation of at least one wire coupled to an end of the bending section. For example, as illustrated in FIGS. 5 and 6, the bending section is bent, as the wire is pulled, in the directions of a first plane 10 or a second plane 20, which have wider widths than side planes. The bending section includes a plurality of elastic members connected with each other.

Figure 3A:
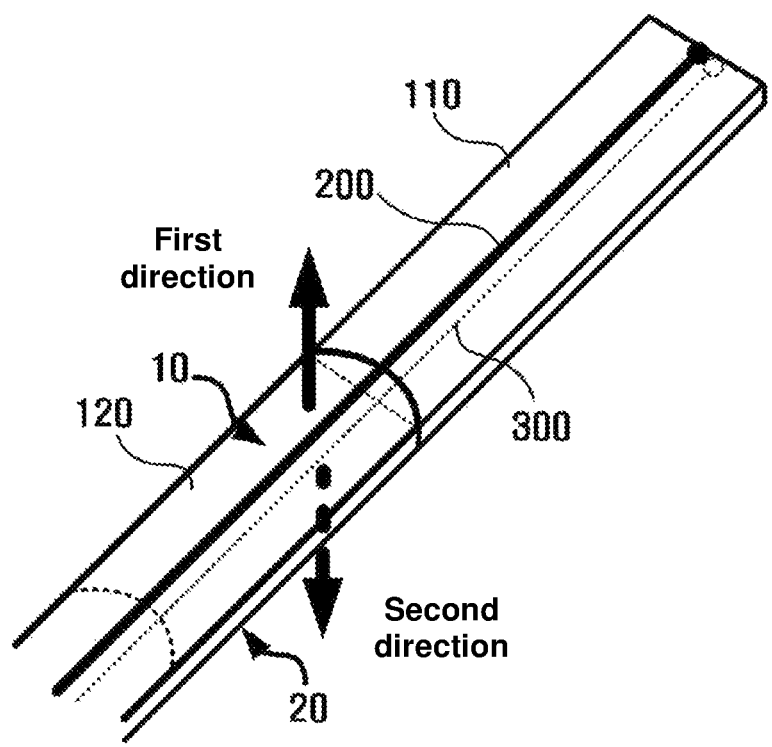

According to some embodiments, the bending section includes a first elastic member 110 and a second elastic member 120, which are connected with each other. In those embodiments, the first elastic member 110 is positioned at the end of the catheter. In some embodiments, the first elastic member 110 has a flat form (see FIGS. 2 and 3A). In some other embodiments, the first elastic member 110 has a form bent with a particular curvature in a direction perpendicular to the forward direction of the catheter. That is, in such embodiments, the first elastic member 110 is curved with a particular radius of curvature to protrude toward a particular direction (see FIG. 4). The second elastic member 120 is connected with the first elastic member 110 and is provided in a form bent with a particular curvature in a direction perpendicular to the forward direction of the catheter. That is, in such embodiments, the second elastic member 120 is curved with a particular radius of curvature to protrude toward a particular direction. As further described below, the combination of the first elastic member 110 and the second elastic member 120 can be the combination of a flat form and a curved form, and the combination of forms having different curvatures and different curved directions.

Figure 3B:
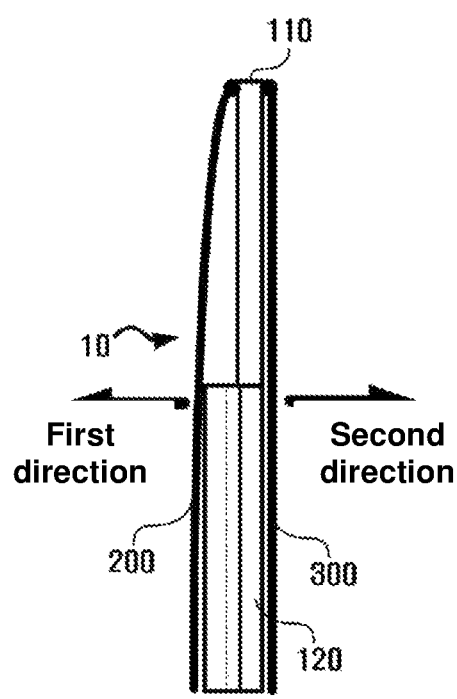

In some embodiments, the first elastic member 110 is coupled to the second elastic member 120 such that the end surface of the first elastic member 110 makes contact with the end surface of the second elastic member 120 (see FIG. 3B). In some other embodiments, the first elastic member 110 is coupled to the second elastic member 120 such that the first elastic member 110 overlaps with the second elastic member 120. The coupling manner between the first elastic member 110 and the second elastic member 120 employs various manners of using an adhesive or of surrounding the connection part between the first elastic member 110 and the second elastic member 120 with a coupling member.

According to some embodiments of a bending section at which the first elastic member 110 is connected with the second elastic member 120, as illustrated in FIG. 2 or FIG. 3, the bending section is formed as the first elastic member 110 is provided in the flat form and the second elastic member 120 is provided in the form bent with a particular curvature in a direction perpendicular to the forward direction of the catheter (i.e., the second elastic member 120 is curved with the particular radius of curvature to protrude toward a specific direction). In some embodiments, the end of the first elastic member 110 and the end of the second elastic member 120 are coupled to each other throughout the whole widths of the first elastic member 110 and the second elastic member 120 (see FIG. 2). In some other embodiments, only a part of the end of the first elastic member 110 and only a part of the end of the second elastic member 120 are coupled to each other, without changing shapes of the ends of the first elastic member 110 and the second elastic member 120.

Figure 4:
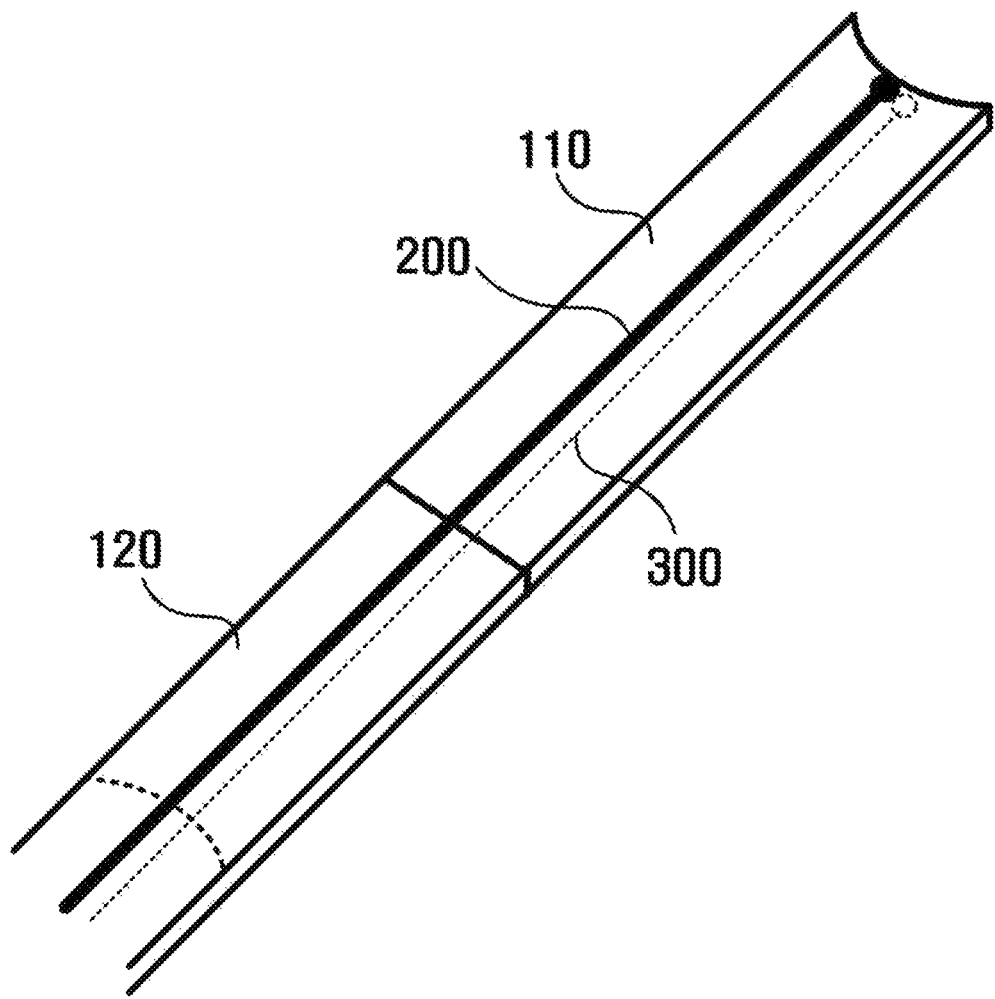
FIG. 4 is a view illustrating a bending section in which a first elastic member and a second elastic member having opposite bending directions are connected with each other, according to some embodiments of the present disclosure.

According to some embodiments of a bending section in which the first elastic member 110 is connected with the second elastic member 120, as illustrated in FIG. 4, the bending section is formed as the first elastic member 110 is provided in the form bent with a particular curvature in a direction perpendicular to the forward direction of the catheter (i.e., the first elastic member 110 is curved with a first radius of curvature to protrude toward a first direction), and the second elastic member 120 is provided in the form bent in a direction opposite to the direction of the first elastic member 110 or bent with a different radius of curvature (i.e., the second elastic member 120 is curved with the second radius of curvature to protrude toward a second direction). In this case, in some embodiments, the end of the first elastic member 110 and the end of the second elastic member 120 are coupled to each other while being deformed such that the whole widths of the first elastic member 110 and the second elastic member 120 make contact with each other (see FIG. 2). In some other embodiments of this case, only a part of the end of the first elastic member 110 and only a part of the end of the second elastic member 120 are coupled to each other, without changing shapes of the ends of the first elastic member 110 and the second elastic member 120. That is, the shapes of the ends of the first elastic member 110 and the second elastic member 120 are maintained.

The first wire 200 is connected with one surface (e.g., the first plane 10) of the first elastic body 110. The second wire 300 is connected with the opposite surface of the first elastic member 110 to the surface with which the first wire 200 is connected (e.g., the second plane 20). In some embodiments, the first wire 200 and the second wire 300 are connected with corresponding positions of the first plane 10 and the second plane 20 (i.e., points at the same distance from the ends of the bending section or points at the ends of the bending section). Further, according to some other embodiments, the first wire 200 and the second wire 300 are connected with different points (i.e., at different distances from the ends of the bending section), depending on the bending forms of the catheter. Accordingly, in some embodiments, as the first wire 200 is pulled, the bending section is pulled in the direction of the first plane 10, so the bending section is bent in the direction of the first plane 10 (e.g., in the first direction). As the second wire 300 is pulled, the bending section is pulled in the direction of the second plane 20 (e.g., in the second direction). In other words, the first wire 200 is bent in the first direction of the catheter through the pulling operation, and the second wire 300 is bent in the second direction of the catheter through the pulling operation.

The tube 600, which surrounds an outer portion the catheter, contains the first elastic member 110, the second elastic member 120, the first wire 200, and the second wire 300. The bending section is provided at the end, in which the catheter has to be bent, of the tube 600. In addition, the first wire 200 and the second wire 300 are pulled inside the tube 600, and return to an original state, due to the elasticity of the bending section. The tube 600 is configured to be inserted into the human body from outside the human body such that the bending portion of the catheter (i.e., the catheter portion including the bending section) reaches the inner part of the human body, which is to be subject to surgery or procedure.

In some embodiments, the bending section is bent in different forms when bent in the first direction and in the second direction, as the first elastic member 110 and the second elastic member 120 having mutually different bending degrees are connected with each other. For example, when the first elastic member 110 in the flat form and the second elastic member 120 bent with the particular curvature are coupled to each other as illustrated in FIG. 3, and when the first wire 200 is pulled in the first direction (e.g., the direction of the first plane 10 corresponding to the convex surface of the second elastic member 120) as illustrated in FIG. 5, the second elastic member 120 is not bent, but only the first elastic member 110 is bent. To the contrary, as illustrated in FIG. 6, when the second wire 300 is pulled in the second direction (e.g., in the direction of the second plane 20 that the second elastic member 120 is curved), both the first elastic member 110 and the second elastic member 120 are bent. Accordingly, in some embodiments, when the bending section is bent in the first direction by the first wire 200 and bent in the second direction by the second wire 300, the bending section is started to be bent at different points, so mutually different curvatures are formed In detail, as the first elastic member 110 and the second elastic member 120, which are different from each other in bending curvature or bending direction, are connected with each other to form the bending section, the catheter has different start points in bending in the first direction and the second direction. When the catheter is bent in the first direction, the catheter is bent from a boundary point between the first elastic member 110 and the second elastic member 120 because the second elastic member 120 is not bent. To the contrary, when the catheter is bent in the second direction, the second elastic member 120 is first bent because the first elastic member 110 and the second elastic member 120 are bent together (see FIG. 11).

Figure 11A:
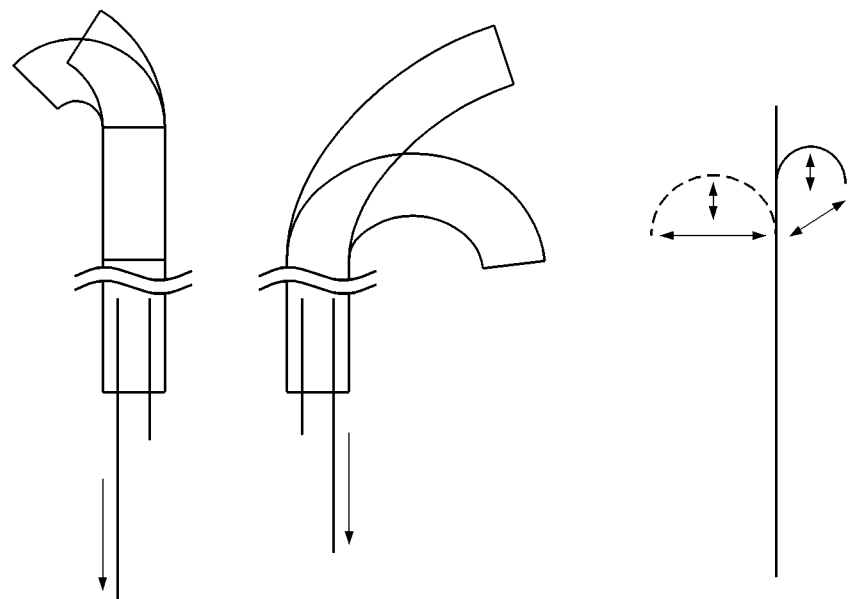
FIG. 11 A is a view illustrating the difference between bending forms of a bending section when the bending section is bent in a first direction and a second direction, according to some embodiments of the present disclosure.
FIG. 11B is a view illustrating an exemplary usage in a cardiac arrhythmia surgery, according to some embodiments of the present disclosure.

Accordingly, in some embodiments, as illustrated in FIG. 11, when the catheter is bent in the first direction, as only the first elastic member 110 is bent, the end of the catheter easily reaches an area close to the entrance path of the catheter. When the catheter is bent in the second direction, as the first elastic member 110 and the second elastic member 120 are bent together, the end (for example, an electrode 700 provided at the end of the catheter as described below) of the catheter reaches a point far away from the entrance path of the catheter. For example, to perform an operation on a part close to the entrance area of the catheter (i.e., to allow the end of the catheter to reach an area close to the entrance path of the catheter), the bending section is bent from the intermediate portion thereof (i.e., the shorter section is bent), so the length of the wire to be pulled is shortened.

In addition, the catheter may be variously bent as the combination of the elastic members is variously made. In some embodiments, the catheter is variously moved due to the lengths of the first elastic member 110 and the second elastic member 120, the difference between curvatures (i.e., bending degrees) of the first elastic member 110 and the second elastic member 120, and/or the bending directions (i.e., the curving directions) of the first elastic member 110 and the second elastic member 120. For example, as the difference in length between the first elastic member 110 and the second elastic member 120 is increased, the difference between curvatures in the first direction bending and the second direction bending is also increased. In addition, for example, in the state that the first elastic member 110 is connected with the second elastic member 120 such that the first elastic member 110 is convex in the direction of the first plane 10 (i.e., the first elastic member 110 is curved to be convex in the first direction), and the second elastic member 120 is convex in the direction of the second plane 20 (i.e., the second elastic member 120 is curved to be convex in the second direction), when the catheter is manipulated to be bent in the specific direction, the catheter has the structure that only one of the first elastic member 110 and the second elastic member 120 is bent.

Figure 9:
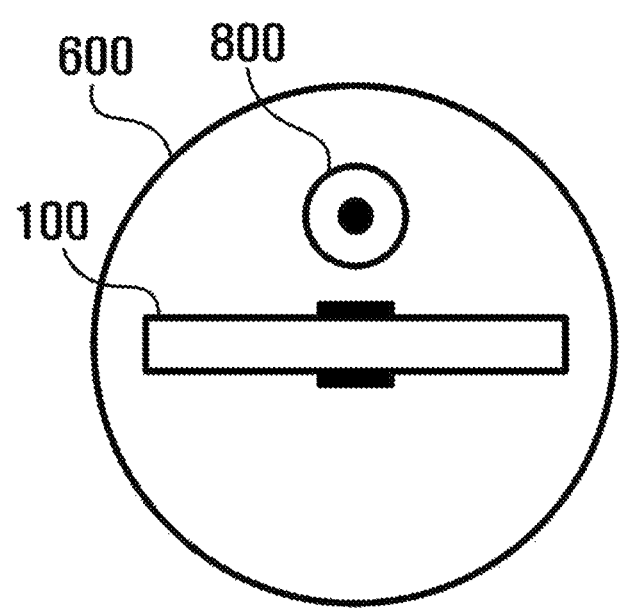
FIG. 9 is a front view illustrating a catheter according to some embodiments of the present disclosure.

In addition, according to some other embodiments, the catheter further includes an endoscope 800. The endoscope 800 passes through the tube 600 as illustrated in FIG. 9. For example, the endoscope 800 is inserted together with the tube 600 when the catheter is inserted in the state that the lens of the endoscope 800 is disposed at the end of the catheter. Accordingly, a medical team may check even an area close to the entrance path of the catheter using the endoscope 800 as the catheter is bent with various curvatures.

Figure 7:
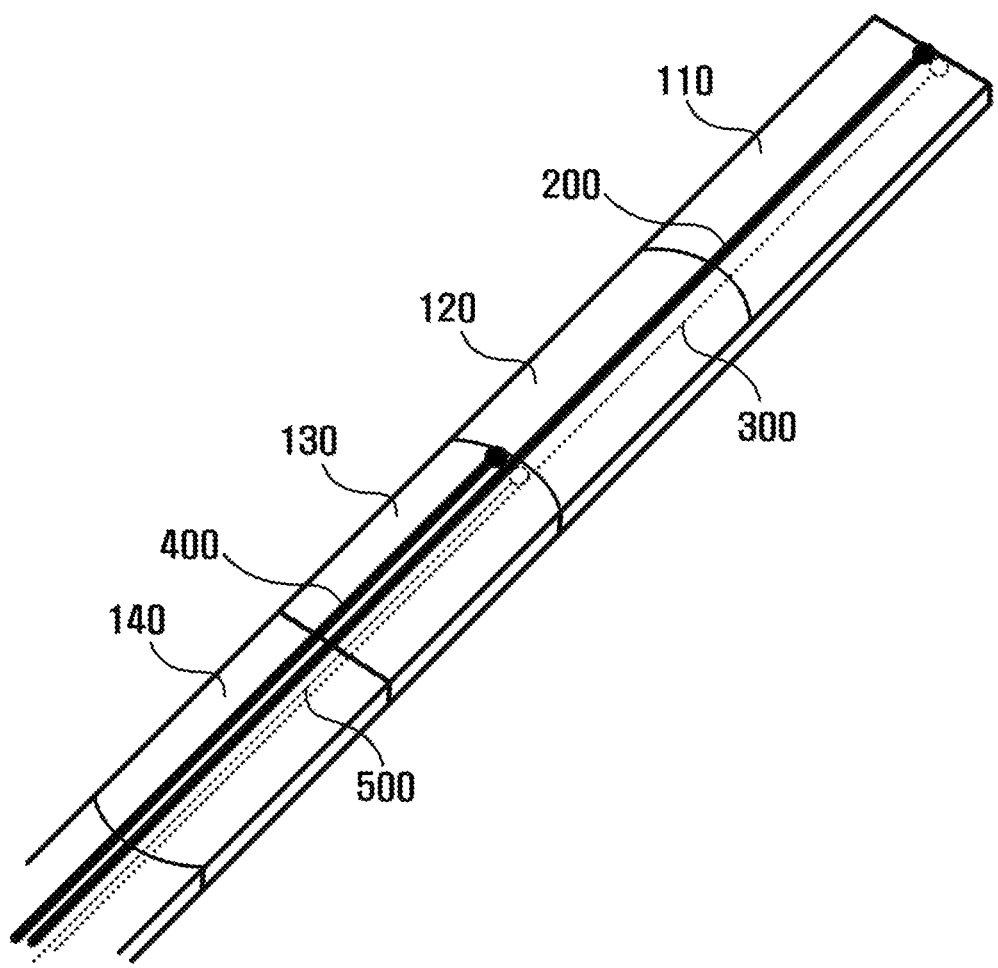
FIG. 7 is a view illustrating a bending section further including a third elastic member and a fourth elastic member, according to some embodiments of the present disclosure.

In addition, according to some other embodiments, as illustrated in FIG. 7, the catheter further includes a third elastic member 130 connected with the second elastic member 120 and flat or bent with a particular curvature in a direction perpendicular to the forward direction of the catheter (i.e., the elastic member 130 being provided to be curved with a particular curvature (e.g., a third radius of curvature) to protrude toward a particular direction). In these embodiments, the catheter further includes a fourth elastic member 140 connected with the third elastic member 130 and bent in a direction opposite to the third elastic member 130 or bent with a different curvature (i.e., the fourth elastic member 140 being curved with a particular radius of curvature (that is, a fourth radius of curvature) different from the third radius of curvature to protrude toward a particular direction. In these embodiments, the catheter further includes a third wire 400 connected with one surface of the third elastic member 130, and a fourth wire 500 connected with an opposite surface to the surface connected with the third wire 400 of the third elastic member 130. In these embodiments, a first bending section at which the first elastic member 110 is connected with the second elastic member 120 is adjusted using the first wire 200 and the second wire 300, and a second bending section, which is formed as the third elastic member 130 and the fourth elastic member 140 are connected with each other and connected with the first bending section, is adjusted using the third wire 400 and the fourth wire 500. Accordingly, the bending section (at which the first bending section is connected with the second bending section) of the catheter is bent in various forms. For example, the first wire 200 and the second wire 300 are pulled with particular strength, and the third wire 400 and the fourth wire 500 are pulled with strength for preventing the second bending section from being bent as the first wire 200 or the second wire 300 is pulled. Accordingly, in this case, only the first bending section is bent. Alternatively, in another case, as force is applied only to the third wire 400 or the fourth wire 500 and not applied to the first wire 200 and the second wire 300, the catheter is bent at the second bending section.

In addition, according to some embodiments, the catheter further includes a handling part to control the first wire 200 and the second wire 300 to be bent in the first direction or the second direction. In these embodiments, as the first wire 200 and the second wire 300 are connected with the handling part, and a user (that is, a medical team) handles the handling part provided in the catheter, the first wire 200 and the second wire 300 are adjusted to be bent in the first direction or the second direction.

Figure 8:
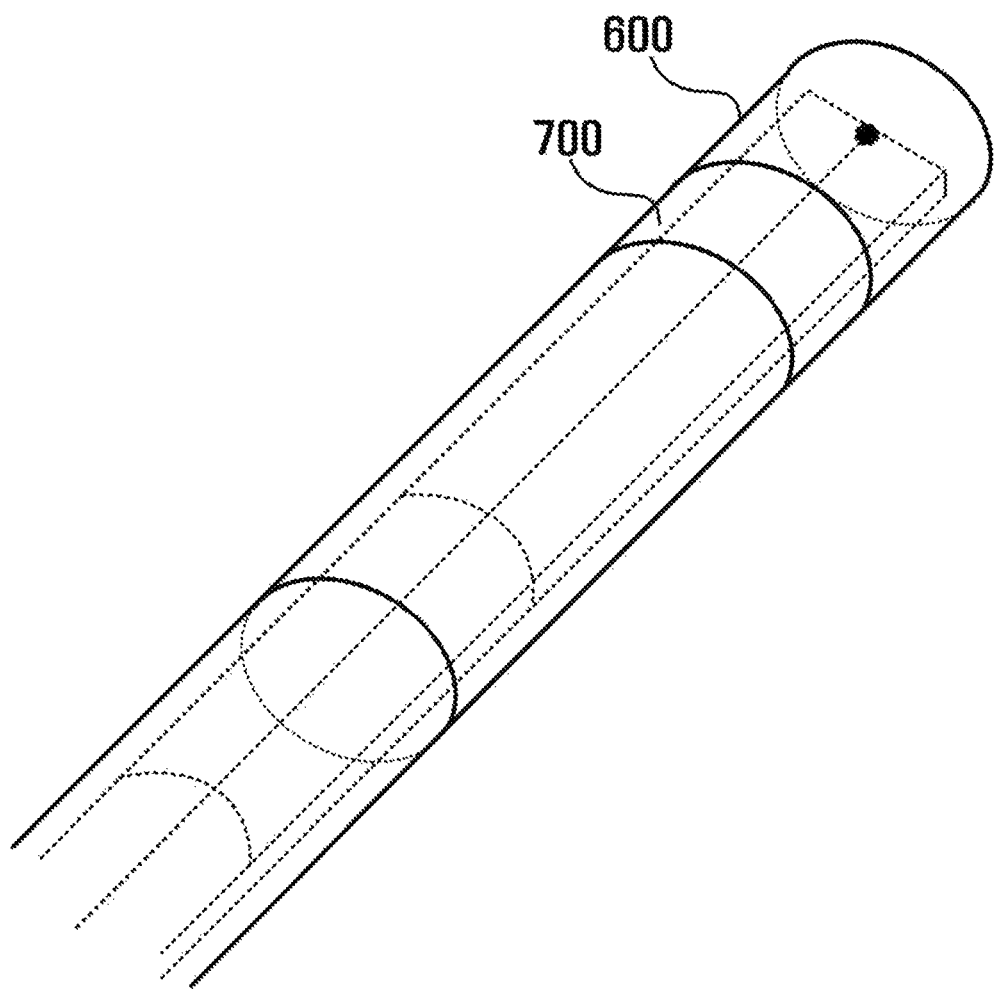
FIG. 8 is a view illustrating a tube provided on a surface thereof with an electrode, according to some embodiments of the present disclosure.

In addition, according to some embodiments, as illustrated in FIG. 8, an electrode 700 that is exposed to the outside of the catheter is included. The catheter measures the electrical signal at a particular point in the human body through the electrode 700 or applies an electrical stimulus to the particular point. As the catheter is bent with various curvatures due to the bending section of the catheter, the medical team allows the electrode 700 to easily reach a desired position in an inner part of the human body.

Further, in some embodiments, the first wire 200 or the second wire 300 includes an electric wire connected with the electrode 700. In these embodiments, the first wire 200 and the second wire 300 corresponding to electric wires are connected with a particular point of the bending section and are connected with an electric wire to connect the particular point with the electrode 700 disposed on the surface of the catheter. Accordingly, in these embodiments, the wire passing through the tube 600 to be connected with the electrode 700 is reduced. When several bending sections (e.g., the first bending section and the second bending section) are connected, the number of the wires is increased, so the inner space of the tube 600 is narrowed. Accordingly, in these embodiment, the number of unit bending sections connected with each other is increased by reducing the number of electric wires inside the tube 600 by integrating the wires and the electric wires.

Figure 10:
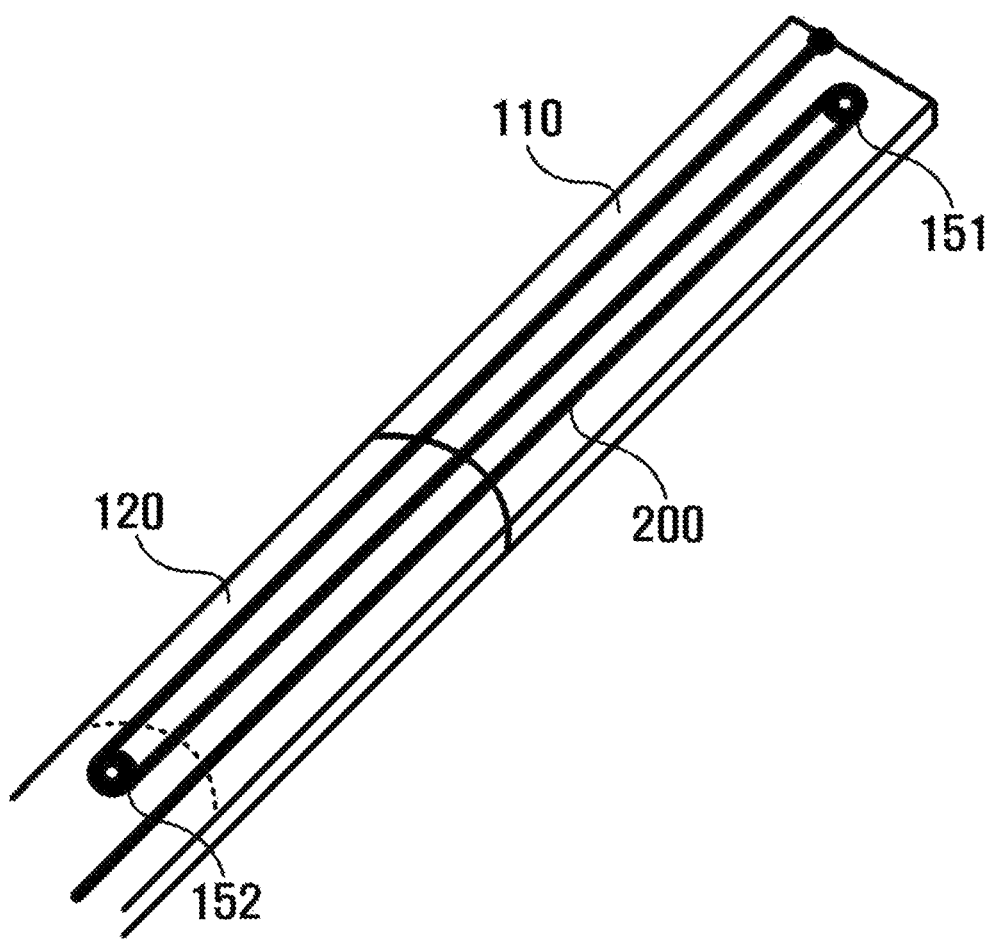
FIG. 10 is a view illustrating a catheter including pulleys, according to some embodiments of the present disclosure.

In addition, according to some embodiments, as illustrated in FIG. 10, the first elastic member 110 and the second elastic member 120 include pulleys 151 and 152 provided on each of the first plane 10, which is a surface connected with the first wire 200, and the second plane 20 which is a surface connected with the second wire 300. The number of pulleys disposed on one surface corresponds to the number of pulleys disposed on the other surface. In these embodiments, the first elastic member 110 and the second elastic member 120 include the pulleys 151 and 152 at one side of the first plane 10 of the first elastic member 110 and at one side of the first plane 10 of the second elastic member 120, such that the number of the pulleys 151 and 152 in the first elastic member 110 corresponds to the number of the pulleys 151 and 152 in the second elastic member 120 (for example, each of the first elastic member 110 and the second elastic member 120 includes one pulley 151 or 152). In some other embodiments, the number of the pulleys 151 and 152 provided on the first plane 10 is different from the number of the pulleys 151 and 152 provided on the second plane 20. In some embodiments, the pulleys 151 and 152 are provided at parts, which are opposite to the coupling part between the first elastic member 110 and the second elastic member 120, of the first elastic member 110 and the second elastic member 120 such that the pulleys 151 and 152 are provided at opposite ends of the bending section.

In some embodiments, the first wire 200 is alternately wound around the pulleys 151 and 152 provided on the first planes 10 of the first elastic member 110 and the second elastic member 120, and the second wire 300 is alternatively wound around the pulleys 151 and 152 provided on the second plane 20 of the first elastic member 110 and the second elastic member 120. In these embodiments, the principle of the movable pulley is applied to the first wire 200 and the second wire 300, so the force is applied to the bending section. Thus, a force greater than the force applied from the outside is transferred to the bending section. Accordingly, even if stiffness is weak in an area, which the bending section is not provided, of the tube 600, the influence exerted by the force from the handling of the bending section may be reduced.

A surgical medical device according to some embodiments of the present disclosure includes: a catheter; and a driving device. The catheter has been described above through the description of the catheter according to some embodiments of the present disclosure.

The driving device is provided outside the catheter (i.e., disposed outside the human body), and controls the degree of pulling of the first wire 200 and the second wire 300 to control bending in the first direction or the second direction. In these embodiments, when the medical team inputs a desired bending state, the driving device controls the first wire 200 and the second wire 300 to achieve the desired bending state based on the calculation result.

According to some embodiments of the present disclosure, the driving device includes a user input unit; a control unit; a first wire driving unit; and a second wire driving unit. The user input unit receives a request for controlling a catheter from a user. The control unit stores a control condition of the first wire 200 and the second wire 300 corresponding to the request for controlling the catheter and transmits the request for controlling the catheter to the first wire driving unit and the second wire driving unit.

In some embodiments, the first wire driving unit is connected with the first wire 200 of the catheter, and the second wire driving unit is connected with the second wire 300 of the catheter. The first wire driving unit and the second wire driving unit apply force to the first wire 200 and the second wire 300 corresponding to the request for control. In some embodiments, the first wire driving unit and the second wire driving unit correspond to rotation motors. In addition, various units capable of pulling the wires may be applied to the first wire driving unit and the second wire driving unit.

In addition, according to some embodiments, the surgical medical device further includes a third elastic member 130, a fourth elastic member 140, a third wire 400 and a fourth wire 500. In these embodiment, the third elastic member 130 connected with the second elastic member 120 has a flat form or bent form with a particular curvature in a direction perpendicular to the forward direction of the catheter (i.e., the elastic member 130 being provided to be curved with a particular curvature (e.g., the third radius of curvature) to protrude toward a particular direction). In these embodiments, the fourth elastic member 140 connected with the third elastic member 130 has a bent form in a direction opposite to the third elastic member 130 or a bent form with a different curvature (i.e., the fourth elastic member 140 being curved with a particular radius of curvature (e.g., the fourth radius of curvature) different from the third radius of curvature to protrude toward a particular direction. In these embodiments, the third wire 400 connected with one surface of the third elastic member 130, and the fourth wire 500 connected with an opposite surface to the surface connected with the third wire 400 of the third elastic member 130. In this case, the driving device controls the first wire 200, the second wire 300, the third wire 400, and the fourth wire 500.

As described above, the inventive concept has various effects.

First, points, at which the catheter is bent in opposite directions, of the bending section are different, so different curvatures are made. Accordingly, the medial team may selectively use the bending form to facilitate access to a specific point in the human body. In addition, as the catheter is bent from the intermediate point of the bending section to allow the end of the catheter to reach the area close to the entrance path (e.g., a heart and blood vessel) of the catheter (that is, only the first elastic member is bent without bending the second elastic member, so the shorter section is bent), the control of the wire for handling the operation of the catheter may become simple in a procedure part.

Figure 11B:
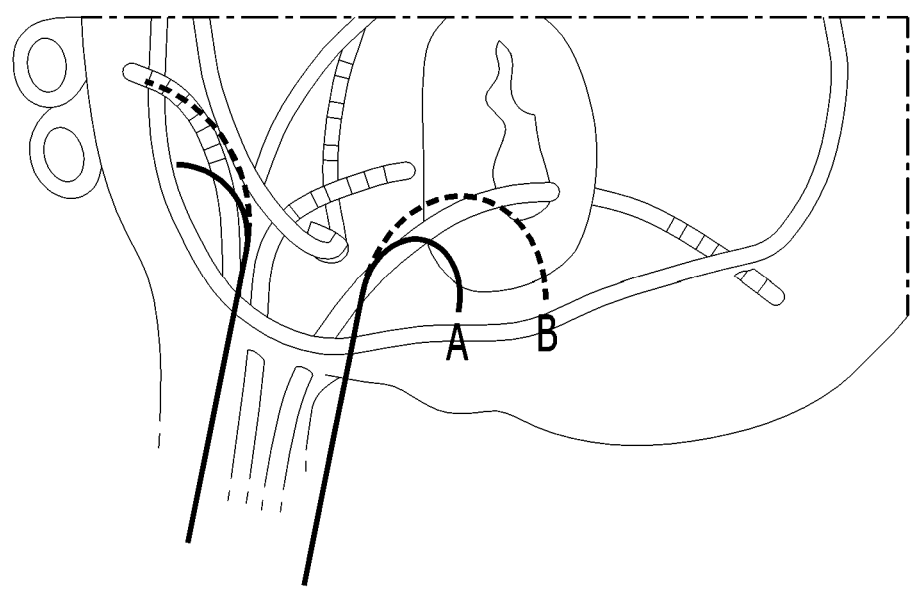

In detail, as illustrated in FIG. 11B, when the catheter introduced through a blood vessel (that is, a specific path to enter a heart) in an arrhythmia procedure is bent to access a point A on an inner wall of the heart, and when the catheter is bent under the same bending condition as that in accessing a point B, the catheter advances excessively and then the wire is pulled more than that in accessing the point B to be bent with a greater curvature. In this case, according to embodiments of the inventive concept, if only the first elastic member included in the bending section is bent and the second bending member is not bent, in the situation that the catheter has to reach a point close to the entrance path of the catheter, the insertion depth (the distance that the catheter advances) of the catheter may be more reduced, and the length of the wire, which has to be pulled, maybe more shorted, as compared to a catheter having one curvature. In other words, according to embodiments of the inventive concept, when compared to the conventional catheter providing a single curvature, the depth and the curvature may be more simply adjusted to reach a procedure point.

Second, various bending forms may be provided as elastic members are variously combined. The catheter may be variously moved based on the lengths of the first elastic member 110 and the second elastic member 120, the difference between curvatures (bending degrees) of the first elastic member 110 and the second elastic member 120, or the bending directions (that is, the curving directions) of the first elastic member 110 and the second elastic member 120.

Third, a conventional catheter for realizing multiple curvatures is difficult to be manufactured in a smaller size since materials having different elasticity has to be added or the thickness of the catheter has to be adjusted so as to form different curvatures depending on directions. To the contrary, in the catheter having multiple curvatures according to embodiments of the inventive concept, the multiple curvatures may be implemented depending on the shapes of the catheter without the additional components. In particular, according to embodiments of the inventive concept, various catheter motions may be realized as several unit bending sections are connected with each other, when the number of the motions which has to be provided by the catheter is increased. Accordingly, the size of the catheter is not increased depending on the number of the realized motions.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A catheter comprising:
   a first elastic member positioned at an end portion of the catheter;
   a second elastic member connected with the first elastic member, wherein the second elastic member has a convex shape curved in a direction perpendicular to a forward direction of the catheter with a first radius of curvature, and protruded toward a first direction;
   a first wire connected with a first surface of the first elastic member, and configured to pull the catheter to bend the catheter in the first direction;
   a second wire connected with a second surface of the first elastic member, which is opposite to the first surface, and configured to pull the catheter to bend the catheter in a second direction; and
   a tube containing the first elastic member, the second elastic member, the first wire, and the second wire.

2. The catheter of claim 1, wherein the first elastic member has a flat form.

3. The catheter of claim 1, wherein the first elastic member has a concave shape curved in the direction perpendicular to the forward direction of the catheter with a second radius of curvature, and curved inward toward the second direction.

4. The catheter of claim 1, further comprising:
   an endoscope.

5. The catheter of claim 1, further comprising:
a third elastic member connected with the second elastic member;
a fourth elastic member connected with the third elastic member and curved with a third radius of curvature to protrude toward the first direction or the second direction;
a third wire connected with a first surface of the third elastic member; and
a fourth wire connected with a second surface of the third elastic member, which is opposite to the first surface of the third elastic member.

6. The catheter of claim 5, wherein the third elastic member has a flat form.

7. The catheter of claim 5, wherein the third elastic member is curved with a fourth radius of curvature to protrude toward the first direction.

8. The catheter of claim 5, wherein a first bending section, where the first elastic member is connected with the second elastic member, is configured to be adjusted by the first wire and the second wire, and
wherein a second bending section, where the third elastic member is connected with the fourth elastic member, is configured to be adjusted by the third wire and the fourth wire.

9. The catheter of claim 1, wherein
the first wire and the second wire are configured to be controlled by a handling part, to control the catheter to bend in the first direction or the second direction.

10. The catheter of claim 1, further comprising:
an electrode exposed to an outside of the catheter,
wherein the first wire or the second wire includes an electric wire connected with the electrode.

11. The catheter of claim 1, further comprising a plurality of pulleys, a number of pulleys disposed on one surface corresponds to a number of pulleys disposed on the other surface,
wherein the plurality of pulleys comprises:
first pulleys disposed on the first surface of the first elastic member and a first surface of the second elastic member; and
second pulleys disposed on the second surface of the first elastic member and a second surface of the second elastic member, and
wherein the first wire is alternately wound around the first pulleys, and the second wire is alternatively wound around the second pulleys.

12. The catheter of claim 1, wherein an end of the first elastic member and an end of the second elastic member are coupled to each other throughout whole widths of the first elastic member and the second elastic member.

13. The catheter of claim 1, wherein a part of an end of the first elastic member and a part of an end of the second elastic member are coupled to each other, without changing shapes of the ends of the first elastic member and the second elastic member.

14. A surgical medical device comprising:
a catheter,
wherein the catheter includes:
a first elastic member positioned at an end portion of the catheter;
a second elastic member connected with the first elastic member, wherein the second elastic member has a convex shape curved in a direction perpendicular to a forward direction of the catheter with a first radius of curvature, and protruded toward a first direction;
a first wire connected with a first surface of the first elastic member;
a second wire connected with a second surface of the first elastic member, which is opposite to the first surface;
a tube containing the first elastic member, the second elastic member, the first wire, and the second wire; and
an electrode exposed to an outside of the catheter, and
wherein the catheter is configured to be connected with a driving device, to control pulling degrees of the first wire and the second wire to bend the catheter in the first direction or a second direction, which is opposite to the first direction.

15. The surgical medical device of claim 14, wherein the first elastic member has a flat form.

16. The surgical medical device of claim 14, wherein the first elastic member has a concave shape curved in the direction perpendicular to the forward direction of the catheter with a second radius of curvature, and curved inward toward the second direction.

17. The surgical medical device of claim 14, further comprising:
a third elastic member connected with the second elastic member;
a fourth elastic member connected with the third elastic member and curved with a third radius of curvature to protrude toward the first direction or the second direction;
a third wire connected with a first surface of the third elastic member; and
a fourth wire connected with a second surface of the third elastic member, which is opposite to the first surface of the third elastic member,
wherein the first wire, the second wire, the third wire, and the fourth wire are configured to be controlled by the driving device.

18. The surgical medical device of claim 17, wherein the third elastic member has a flat form.

19. The surgical medical device of claim 17, wherein the third elastic member is curved with a fourth radius of curvature to protrude toward the first direction.

20. The surgical medical device of claim 14, wherein the first wire or the second wire includes an electric wire connected with the electrode.

* * * * *